US008283312B2

(12) United States Patent
Meguid et al.

(10) Patent No.: US 8,283,312 B2
(45) Date of Patent: Oct. 9, 2012

(54) COMPOSITIONS AND METHODS FOR MODULATING BODY WEIGHT AND TREATING OBESITY-RELATED DISORDERS

(75) Inventors: Michael M. Meguid, East Syracuse, NY (US); Susumu Suzuki, Syracuse, NY (US)

(73) Assignee: The Research Foundation of State University of New York, Albany, NY (US)

( * ) Notice: Subject to any disclaimer, the term of this patent is extended or adjusted under 35 U.S.C. 154(b) by 1839 days.

(21) Appl. No.: 11/347,195

(22) Filed: Feb. 3, 2006

(65) Prior Publication Data

US 2006/0293233 A1    Dec. 28, 2006

Related U.S. Application Data

(60) Provisional application No. 60/650,003, filed on Feb. 4, 2005.

(51) Int. Cl.
 *A61K 38/22* (2006.01)
 *A61K 38/00* (2006.01)
 *A61K 38/28* (2006.01)
 *A61P 3/04* (2006.01)
 *A61P 3/10* (2006.01)
 *A61P 7/12* (2006.01)

(52) U.S. Cl. .......................... 514/5.2; 514/6.9
(58) Field of Classification Search ........................ None
See application file for complete search history.

(56) References Cited

U.S. PATENT DOCUMENTS

| | | | |
|---|---|---|---|
| 3,752,888 A | | 8/1973 | Fluckiger et al. |
| 4,210,637 A | * | 7/1980 | Wurtman et al. ............... 514/53 |
| 4,703,108 A | | 10/1987 | Silver et al. |
| 4,774,091 A | | 9/1988 | Yamahira et al. |
| 4,849,141 A | | 7/1989 | Fujioka et al. |
| 4,929,629 A | | 5/1990 | Jeffery |
| 5,604,203 A | * | 2/1997 | Balasubramaniam ......... 514/7.4 |
| 5,643,874 A | | 7/1997 | Bremer et al. |
| 5,912,227 A | * | 6/1999 | Croom et al. .................. 514/1.2 |
| 7,825,090 B2 | * | 11/2010 | Ghigo et al. ................... 514/6.7 |
| 7,959,924 B2 | * | 6/2011 | Bachmann et al. ......... 424/185.1 |

OTHER PUBLICATIONS

Kojima et al. Ghrelin: Structure and Function. Physiol. Rev. Apr. 2005, vol. 85, No. 2, pp. 495-522.*
Adams et al. Effects of Peptide YY[3-36] on Short-Term Food Intake in Mice Are Not Affected by Prevailing Plasma Ghrelin Levels. Endocrinology 2004, published online Jul. 29, 2004. vol. 145, pp. 4967-4975.*
Voisin et al. FUnctional and Molecular Properties of the Human Recombinant Y4 Receptor: Resistance to Agonist-Promoted Desensitization. JPET, 200. vol. 292, No. 2, pp. 628-646.*
Abbott et al. Blockade of the neuropeptide Y Y2 receptor with the specific antagonist BIIE0246 attenuates the effect of endogenous and exogenous peptide YY(3-36) on food intake. Brain Res, May 10, 2005, vol. 1043(1-2), pp. 139-144.*
Liu C.D. et al., "A Novel Synthetic Analog of Peptide YY, BIM-43004, Given Intraluminally, Is Proabsorptive", *Journal of Surgical Research 59* (1):80-84 (1995).
Litvak D.A. et al., "Characterization of Two Novel Proabsorptive Peptide YY Analogs, BIM-43073D and BIM-43004C", *Digestive Diseases and Sciences 44* (3):643-648 (1999).
Kojima M. et al., "Ghrelin is a Growth-Hormone-Releasing Acylated Peptide from Stomach", *Nature 402*:656-660 (1999).
Goumain M. et al., "The Peptide YY-Preferring Receptor Mediating Inhibition of Small Intestinal Secretion is a Peripheral $Y_2$ Receptor: Pharmacological Evidence and Molecular Cloning", *Molecular Pharmacology 60*(1):124-134 (2001).

* cited by examiner

*Primary Examiner* — Marcela M Cordero Garcia
(74) *Attorney, Agent, or Firm* — Scully, Scott, Murphy & Presser, P.C.

(57) ABSTRACT

The present invention relates to compositions and methods for regulating body weight, and for treating conditions associated with obesity, particularly, obesity-related diabetes. The present invention is premised on the discovery that body weight can be effectively regulated by modulating the levels and/or activities of two gut hormones, PYY and ghrelin.

10 Claims, 7 Drawing Sheets

COMPOSITIONS AND METHODS FOR MODULATING BODY WEIGHT AND TREATING OBESITY-RELATED DISORDERS

CROSS REFERENCE TO RELATED APPLICATIONS

The present application claims benefit of U.S. Provisional Application No. 60/650,003 filed Feb. 4, 2005.

FIELD OF THE INVENTION

The present invention relates to compositions and methods for modulating body weight, and for treating obesity and conditions associated with obesity, particularly, diabetes and catabolic conditions.

BACKGROUND OF THE INVENTION

Obesity is a metabolic disorder characterized by excessive accumulation of fat stores in adipose tissue. Obesity is often associated with various pathological conditions or with risks of developing such conditions, e.g., cardiovascular disease, diabetes, cancer, hypertension, among others. In morbid obesity, the most effective method to achieve prolonged weight loss is via surgical intervention (1,2,3). One of the effective operations is the Roux-en-Y gastric bypass (RYGB), which produces durable weight loss. This operation is based on two principles: 1) creating a small gastric pouch to physically limit the size of a meal and thereby induce early satiety, and 2) inserting a short Roux-en-Y alimentary limb of distal small bowel, anastomosed to stomach and to proximal small bowel, to form a short common channel in which food from the pouch mixes with biliary-pancreatic digestive juices (4). The resulting anatomy of the RYGB reduces the amount of food that can be consumed, digested and absorbed, inducing prolonged weight loss (1,2,3). It is axiomatic that the RYGB operation in morbidly obese patients induces weight loss because of the mechanical restriction of the small gastric pouch and because of varying degrees of sub-clinical malabsorption (2,5,6). This notion was strengthened by an early study of eating patterns in 80 patients done 6, 12 and 24 months after RYGB (7). A significant reduction occurred in the amount of food eaten and in the frequency of eating. The authors concluded that gastric bypass "may have had an effect on digestion and absorption as well as the mechanical impairment of food intake secondary to the small gastric pouch".

To understand the mechanisms whereby RYGB induced weight loss, a RYGB model in diet-induced obese Sprague-Dawley rats was developed (6,8,9). Eating patterns were measured using an Automated Computerized Rat Eater Meter. It was reported that meal size (Mz) is significantly smaller in RYGB than in sham operated (SO) obese control rats (6,8). Contrary to the usual physiological response, when MZ was decreased a compensatory increase in meal number (MN) occurred to maintain daily food intake (FI) constant (i.e. FI=MZ×MN) (10), a decrease in MN after RYGB occurred resulting in a net decrease in food intake contributing to weight loss (6,8,9). Since specific nuclei in the hypothalamus regulate MZ and MN, these primary food intake and energy regulating hypothalamic nuclei were also examined in the rat, after RYGB induced weight loss. It was reported that food intake and energy regulating genes are down regulated (12). In a more recent immunohistochemical study, it was demonstrated that clinically relevant food intake neuromediators were reduced after RYGB (11,12,13). The results of these studies suggest that the hypothalamus, which regulates GI hormone secretion via efferent vagal and sympathetic fibers to the GI tract, as well as via hypothalamic neuro-pituitary secretions of hormone precursor, plays a contributory role in decreasing food intake after RYGB. These data, together with both human and rat data, consistently show resolution of type 2 diabetes after RYGB, further suggesting that a hormonal component plays a contributory role in reducing food intake and facilitate protracted weight loss after RYGB (14).

There remains a need for effective compositions and methods for regulating body weight and for treating conditions associated with obesity.

SUMMARY OF THE INVENTION

The present inventors have uniquely recognized that body weight can be effectively regulated by modulating the relative levels and/or activities of two gut hormones, PYY and ghrelin.

In one aspect of the present invention, compositions and methods are provided for reducing body weight or the rate of weight gain in a subject and for treating obesity and consequently obesity-related disorders.

In one embodiment, the present invention provides a pharmaceutical composition that contains an effective amount of a combination of a PYY or a functional analog thereof, and a ghrelin or a functional analog thereof. The PYY or a functional analog thereof and the ghrelin or a functional analog thereof are in such amounts and ratio that upon administration to a subject, the PYY concentration in the subject is significantly increased, while the ghrelin concentration remains at a low physiological level.

In another embodiment, the present invention provides a method for reducing the body weight or the rate of weight gain, or for treating obesity or an obesity-related disorder in a subject, by administering a pharmaceutical composition described hereinabove.

In a further aspect of the present invention, compositions and methods are provided for increasing body weight or decreasing the rate of weight loss in a subject in need thereof.

In one embodiment, the present invention provides a pharmaceutical composition that contains an effective amount of a combination of a PYY antagonist or a PYY receptor antagonist with a relatively high level of ghrelin or a functional analog of ghrelin, wherein the combination stimulates food intake and body weight gain.

In another aspect, the present invention provides a method for increasing the body weight or decreasing the rate of weight loss in a subject, by administering a pharmaceutical composition that contains an effective amount of a combination of a PYY antagonist or a PYY receptor antagonist with a relatively high level of a ghrelin or a functional analog of ghrelin.

BRIEF DESCRIPTION OF THE DRAWINGS

FIG. 5. Gastric emptying rate (5-A) and Intestinal transit time (5-B) in Control and RYGB rats 28 days after surgery. *p<0.05 compared to Control.

DETAILED DESCRIPTION OF THE INVENTION

In work leading up to the present invention, it has been determined in a diet-induced obese RYGB rat model that, after a Roux-en-Y gastric bypass (RYGB) surgery, the level of peptide YY (PYY) significantly increased and remained high, whereas the level of ghrelin decreased and remained low, for extended periods of time. PYY is a gut hormone that inhibits food intake, whereas ghrelin is a gut hormone that stimulates food intake. It is believed that the relative concentrations of these gut hormone observed in RYGB rats result in a decrease in food intake, slower gastric emptying, and longer transit time, which contribute to prolonged weight loss after RYGB. Furthermore, it has been determined that administration of a PYY receptor antagonist with physiological levels of ghrelin to RYGB rats reversed the effects of RYGB, leading to daily and cumulative food intake increases and concomitant weight gain. The administration of physiological levels of ghrelin (60 ng/Kg/day) alone to RYGB rats did not significantly increase food intake or body weight, and the combined administration of a PYY receptor antagonist and ghrelin did significantly increase food intake and weight gain. Therefore, it is believed that the administration of a PYY antagonist or a PYY receptor antagonist and high levels of ghrelin can increase body weight in conditions where weight gain is desirable. Accordingly, the present invention provides compositions and methods for regulating body weight and for treating obesity-related disorders without the need of surgical procedures.

In one aspect of the present invention, compositions and methods are provided for reducing body weight or the rate of weight gain in a subject and for treating obesity and obesity-related disorders.

The term "subject" as used herein, refers to any mammalian subject, particularly a human subject.

The terms "obese" and "obesity", as used herein, are used to refer to a condition in which an animal subject (typically human) has a body mass index (BMI) of greater than 25 kilograms per square meter.

By "obesity-related disorders" and "disorders associated with obesity" are meant conditions that accompany, frequently caused by, obesity, and include, for example, non-insulin dependent diabetes mellitus (NIDDM or type 2 DM), cardiovascular disorders, hypertension, stroke, respiratory problems, sleep apnea, gastroesophageal reflux disease (GERD), cancer and osteroarthritis.

By "treating obesity" is meant reducing, ameliorating, eliminating or preventing obesity in a subject that suffers from obesity or is at risk of becoming obese.

By "treating a disorder associated with obesity" is meant reducing, ameliorating, eliminating or preventing the disorder in a subject that suffers from the disorder or is at risk of developing the disorder as a result of obesity.

In one embodiment, the present invention provides a pharmaceutical composition that contains a combination of a peptide YY (PYY) or a functional analog thereof and a ghrelin or a functional analog thereof, in an amount effective to decrease food intake and body weight. The PYY or a functional analog thereof and the ghrelin or a functional analog thereof in the composition are in such amounts and ratio that upon administration to a subject, the concentration of functional PYY in the subject is significantly increased, while the concentration of functional ghrelin remains at a low physiological level PYY is a 36-residue peptide amide, primarily secreted by the endocrine cells of distal small intestine and colon. PYY is believed to inhibit gastric emptying, gut motility, and food intake (18,19). The human, porcine, dog and rat PYY sequences are described in U.S. Pat. No. 5,604,203. Although PYY obtained from any mammalian species can be used, human PYY is preferred for use in the pharmaceutical composition of the present invention.

By "functional analog of PYY" is meant a compound that shares structural similarities to PYY (e.g., peptide fragments of PYY, derivatives having one or more amino acid insertions, deletions or substitutions, or with one or more substituted side groups) and exhibits a biological activity of PYY, such as inhibition of gastric emptying, inhibition of gut motility, or inhibition of food intake. Functional analogs of PYY have been documented in the art and include PYY$_{3-36}$, PYY$_{22-36}$, BIM-43004 (Liu et al. *J. Surg. Res.* 59(1):80-84, 1995), BIM-43073D (Litvak et al. *Dig. Dis. Sci.* 44(3): 643-48, 1999), BIM-43004C (Litvak et al. 1999). Other examples of functional PYY analogs are described in U.S. Pat. No. 5,604,203. Additional PYY analogs can be designed, selected or otherwise identified using the methods known in the art, these additional PYY analogs can include a peptide consisting of amino acid 3 to 36 of a human PYY, BIM-43073D, N-α-Ac-[Phe$^{27}$]PYY(22-36), N-α-Ac-[TRP27]PYY(22-36), N-α-Ac-[Thi$^{27}$]PYY(22-36), N-α-Ac-[Tyr$^{22}$, Phe$^{27}$]PYY(22-36), [Im-DNP-His$^{26}$]PYY, PYY(22-36), [Ala$^{32}$]PYY(22-36), [Ala$^{23,32}$]PYY(22-36), [Glu$^{28}$]PYY(22-36), N-α-Ac-PYY (22-36), N-α-Ac-[p.Cl-Phe$^{27}$]PYY(22-36), N-α-Ac-[Glu$^{26}$] PYY(22-36), N-α-Ac-[N-Me-Tyr$^{36}$]PYY(22-36), N-α-Myristoyl-PYY(22-36), N-α-Naphthaleneacetyl-PYY(22-36), N-α-Ac-[Phe$^{27}$]PYY(22-36), N-α-Ac-[Bth$^{27}$]PYY(22-36), N-α-Ac-[Bip$^{27}$]PYY(22-36), N-α-Ac-[Nal$^{27}$]PYY(22-36), N-α-Ac-[Tic$^{27}$]PYY(22-36), N-α-Ac-[Phe$^{27}$]PYY(25-36) and N-α-Ac-[Trp$^{27}$]PYY(22-36), PYY(13-36), NPY(13-36).

Ghrelin is a peptide of 28 amino acids, in which the serine 3 residue is n-octanoylated. Human and rat ghrelin amino acid sequences are described in Kojima et al. *Nature* 402 (6762):656-60 (1999). Ghrelin is produced primarily by A cells in the oxyntic glands of the stomach fumdus and proximal small intestine, and its concentration increases significantly before and decreases after each meal. Normally, ghrelin is both vagally and hormonally sensed by the hypothalamic arcuate nucleus where it activates neurons that secrete NPY, to stimulate food intake and promote weight gain (27,28,29). Ghrelin also inhibits release of serotonin in the brain, a substance that generally inhibits food intake (30).

Although ghrelin obtained from any mammalian species can be used, human recombinant ghrelin is preferred for use in the pharmaceutical composition of the present invention.

By "functional analog of ghrelin" is meant a compound that shares structural similarities to ghrelin (e.g., peptide fragments of a ghrelin, derivatives having one or more amino acid insertions, deletions or substitutions, or with one or more substituted side groups) and exhibits a biological activity of ghrelin. Functional ghrelin analogs can be designed, selected or otherwise identified using the methods known in the art.

The amount of a PYY or a functional analog thereof and the amount of a ghrelin or a functional analog thereof are effective to decrease food intake in the subject, thereby decreasing body weight or the rate of weight gain in a subject. Generally speaking, the pharmaceutical composition can contain a PYY or a functional analog thereof in an amount of about 2 nmol to about 4 nmol per square meter of body surface area per dose, in combination with a ghrelin in an amount of about 1.0 fmol to about 2.0 fmol per square meter of body surface area per dose. The ratio of the PYY or a functional analog relative to the ghrelin or a functional analog in the composition thereof is generally in the range of 2:1 (nmol/fmol) to 10:1 (nmol/fmol), preferably about 4:1 (nmol/fmol).

According to the present invention, the pharmaceutical compositions described above can also include other agents suitable for reducing body weight. Examples of suitable agents include anti-obesity agents such as orlistat (U.S. Pat. No. 5,643,874), sibutramine (U.S. Pat. No. 4,929,629), bromocriptine (U.S. Pat. No. 3,752,888), ephedrine, leptin, and pseudoephedrine.

The pharmaceutical compositions of the present invention can include a pharmaceutically acceptable carrier. As used herein, a pharmaceutically acceptable carrier includes solvents, dispersion media, isotonic agents and the like. Except insofar as any conventional media, agent, diluent or carrier is detrimental to the recipient or to the therapeutic effectiveness of the active ingredients contained therein, its use in the pharmaceutical compositions of the present invention is appropriate. The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof.

In a specific embodiment, the carrier for use in the pharmaceutical composition of the present invention is a controlled release material, which allows the slow release of the active ingredients admixed therein. Examples of controlled release material include, but are not limited to, sustained release biodegradable formulations described in U.S. Pat. No. 4,849,141, U.S. Pat. No. 4,774,091, and U.S. Pat. No. 4,703,108, all of which are incorporated herein by reference.

In accordance with the present invention, the active ingredients of the present pharmaceutical compositions can be combined with the carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like.

In still another embodiment, a pharmaceutical composition described hereinabove is administered to a subject for reducing the body weight or the rate of weight gain, or for treating obesity or an obesity-related disorder.

The pharmaceutical compositions of the present invention can be administered to a subject by standard routes, including the oral, ophthalmic, nasal, transdermal, and parenteral (e.g., intravenous, intraperitoneal, intradermal, subcutaneous or intramuscular) routes. In addition, the composition can be delivered through an implanted device or controlled release material. Preferred routes of administration include subcutaneous, intraperitoneal, transdermal patch, and particularly, oral administration.

In a further aspect of the present invention, compositions and methods are provided for increasing body weight or decreasing the rate of weight loss in a subject.

Subjects that will be benefited by the compositions and methods in this aspect of the present invention include those individuals who suffer from a wasting disorder (e.g., wasting syndrome, cachexia, sarcopenia) which cause unhealthy loss of weight, and can be the result of inadequate intake of food and/or metabolic changes related to illness and/or the aging process. Individuals suffering a wasting disorder can include elderly individuals, AIDS and cancer patients, as well as patients following extensive surgery or having chronic infections, immunologic diseases, hyperthyroidism, extraintestinal Crohn's disease, psychogenic disease, chronic heart failure or other severe trauma.

In one embodiment, the present invention provides a pharmaceutical composition that contains a combination of a PYY antagonist or a PYY receptor antagonist, with a ghrelin or a functional analog of ghrelin, in an amount effective to increase body weight or decrease the rate of weight loss in a subject.

By "PYY antagonist" is meant a compound that specifically inhibits the expression, release, or activity of PYY in a subject, or reduces the stability of PYY in the subject. By "PYY receptor antagonist" is meant a compound that specifically inhibits the activity of a PYY receptor in a subject. Examples of PYY receptor antagonists have been described in Goumain et al., *Mol. Pharmacol.* 60: 124-134 (2001), such as B11E0246. Those skilled in the art can design, select or otherwise identify a PYY antagonist or a PYY receptor antagonist using the methods known in the art.

A PYY receptor antagonist and a ghrelin or a functional analog thereof are in such amounts and ratio effective to increase food intake in the subject, thereby increasing body weight or the rate of weight gain in a subject. Generally speaking, the pharmaceutical composition can contain an antagonist of a PYY receptor in an amount of about 280 nmol per day to about 440 nmol per day per dose, in combination with a ghrelin of a functional analog thereof in an amount of about 10 fmol to about 20 fmol per dose. The ratio of the PYY antagonist or PYY receptor antagonist relative to the ghrelin of a functional analog thereof is generally in the range of about 40:1 (nmol/fmol) to about 10:1 (nmol/fmol), preferably about 20:1 (nmol/fmol).

According to the present invention, the pharmaceutical compositions for increasing body weight can also include other agents suitable for increasing- or retaining body weight, such as an anabolic steroid, a growth hormone, erythropoietin, a cytokine, or an anti-cytokine agent. Such pharmaceutical compositions of the present invention can also include any one of the pharmaceutically acceptable carriers described herein above.

In another embodiment, a pharmaceutical composition of the present invention suitable for increasing or retaining body weight is administered to a subject for increasing the body weight or decreasing the rate of weight loss. The pharmaceutical composition can be administered to a subject by standard routes, including the oral, ophthalmic, nasal, transdermal, and parenteral (e.g., intravenous, intraperitoneal, intradermal, subcutaneous or intramuscular) routes. In addition, the composition can be delivered through an implanted device or controlled release material. Preferred routes of administration include subcutaneous, intraperitoneal, transdermal patch, and particularly, oral administration.

This invention is further illustrated by the following examples, which are not to be construed in any way as imposing limitations upon the scope of the invention. All the publications referred to in the present disclosure are incorporated herein by reference.

Example 1

Vagal Celiac Efferent Activity to Upper Gastrointestinal Organs After Gastric Bypass To test the hypothesis that weight loss after RYGB could be due to diminished feedback from hypothalamic food intake regulatory centers to the UGI organs via vagal celiac efferent activity, diet-induced obese rats that had either a RYGB with preservation of the vagus or a sham operation (SO obese) were examined. 100 days after operation, when RYGB (545±43 g [M±SE]) had lost 31% body weight as compared to SO obese rats (788±34 g), a branch of the vagal efferent celiac nerves that innervate the gastric pouch and the alimentary limb of the RYGB were isolated under general anesthesia using intra-peritoneal injection of urethane. Vagal efferent celiac nerve firing rates were measured via recording electrodes before and for 180 min after a 5% glucose in 5 ml water gavage. Differences in firing rates were evaluated using ANOVA and t-test. In SO obese rats, 60 min after oral glucose gavage, vagal celiac efferent discharge rates increased from 71±3 impulses/5 sec to 103±13 impulses/5 sec ($p<0.05$). This effect persisted for 180 min. In contrast, there was no change in firing rates in RYGB rats (from 61±2 impulses/5 sec to 65±6 impulses/5 sec). The failure of vagal efferent activity in respond to a glucose load suggests that the significant weight loss after RYGB in diet induced obese rats is at least in part due to decreased input from the hypothalamic food intake regulatory centers to the UGI organs that activate gastric motility and the secretion of GI enzymes and hormones.

Example 2

Methods

Preoperative Procedures: Seventy-two 3-4 week-old male Sprague Dawley pups (Charles River, Wilmington, Mass.), weighing 70.8±0.7 g (M±SE), were acclimated to study conditions: 12-12-hours light-dark cycle (lights on at 6:00 am), 26±1° C. room temperature, and 45% humidity. Diet-induced obesity was achieved using a high fat diet (HFD, D12266, Research Diets®, New Brunswick, N.J.) for 16 weeks (6). The HFD consisted of 4.5 kcal/g, of which 21% of metabolizable energy content was protein, 31% fat and 48% carbohydrate (consisting 50% sucrose). The rats ate ad libitum and had municipal tap water. After 16 weeks on the HFD, the 72 diet induced obesity rats were stratified according to body weight (BW) and equally divided into: 1) Sham operated GI intact obese rats (SO Obese), which continued to eat ad libitum; 2) Roux-en-Y Gastric Bypass rats (RYGB); and 3) Sham-operated GI intact pair fed rats (PF).

To measure upper GI motility and transit time, 24 different male Sprague Dawley rats [weight: 640±13 g (M±SE); Charles River, Wilmington, Mass.] were purchased and fed regular chow diet (Rat Chow diet #5008; Ralston Purina, St Louis, Mo.). After the acclimation, these rats also stratified according to BW and equally divided into: 1) Sham operated GI intact control rats (Control) and 2) RYGB rats. Prior to operation rats were food deprived for 16 hours and were anesthetized with ketamine and xylazine mixture (150:30 mg/mL) via intraperitoneal injection (0.8 mL/kg) (6). Gastric emptying rates were studied in one half of each group while transit time was measured in the other half.

Surgical Procedures: The procedures for the RYGB and the sham operation were previously described (6). Briefly, a triple rows of titanium staple lines (ENDOPATH ELC 35 mm, Ethicon®, Cincinnati, Ohio) were placed between the gastric lesser and greater curvature to create a 20% gastric pouch. The vagus nerves were preserved. The jejunum was divided 30 cm below the ligament of Treitz and a gastrojejunostomy was created, and a side-to-side jejuno-jejunostomy was done 10 cm below the gastrojejunostomy. For the sham operation, a mid-line abdominal incision was made and the stomach, esophagus and small bowel were manipulated for the same duration required for the RYGB. The celiotomy incision was closed. Post-operative care was provided as previously described in detail (6). Liquid diet (Boost Plus®, Mead Johnson, Evansville, Ind.) was provided for the first 7 days followed by regular chow.

Figure 1:
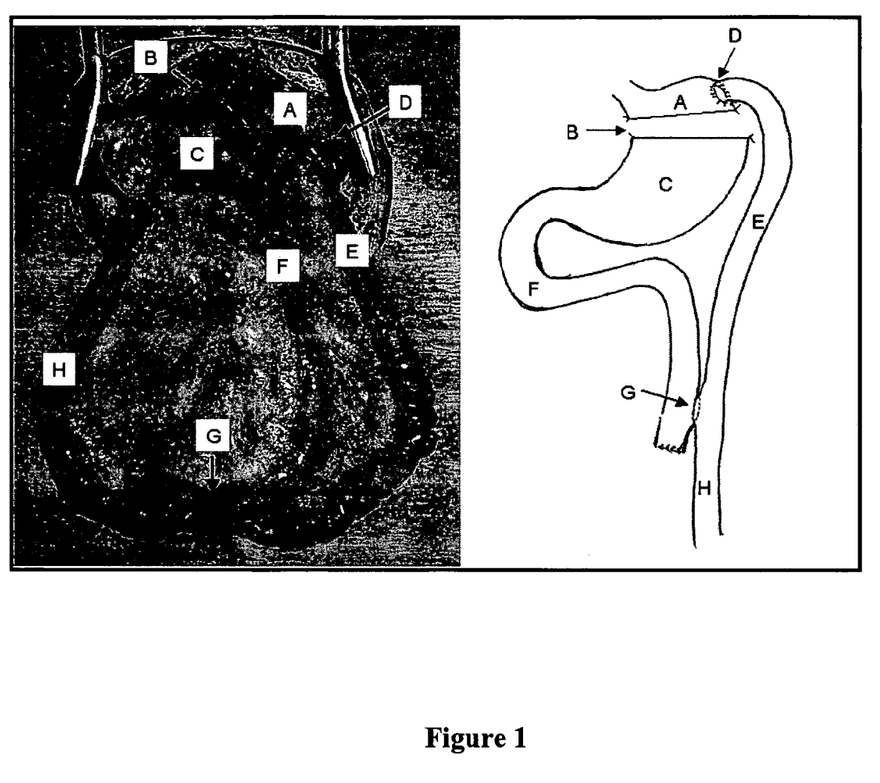
FIG. 1. Roux-en-Y gastric bypass in the rat model. A, pouch; B, staple lines; C, remaining stomach; D, gastrojejunostomy; E, alimentary limb; F, biliary-pancreatic limb; G, jejuno-jejunostomy; H, common channel.
Figure 2:
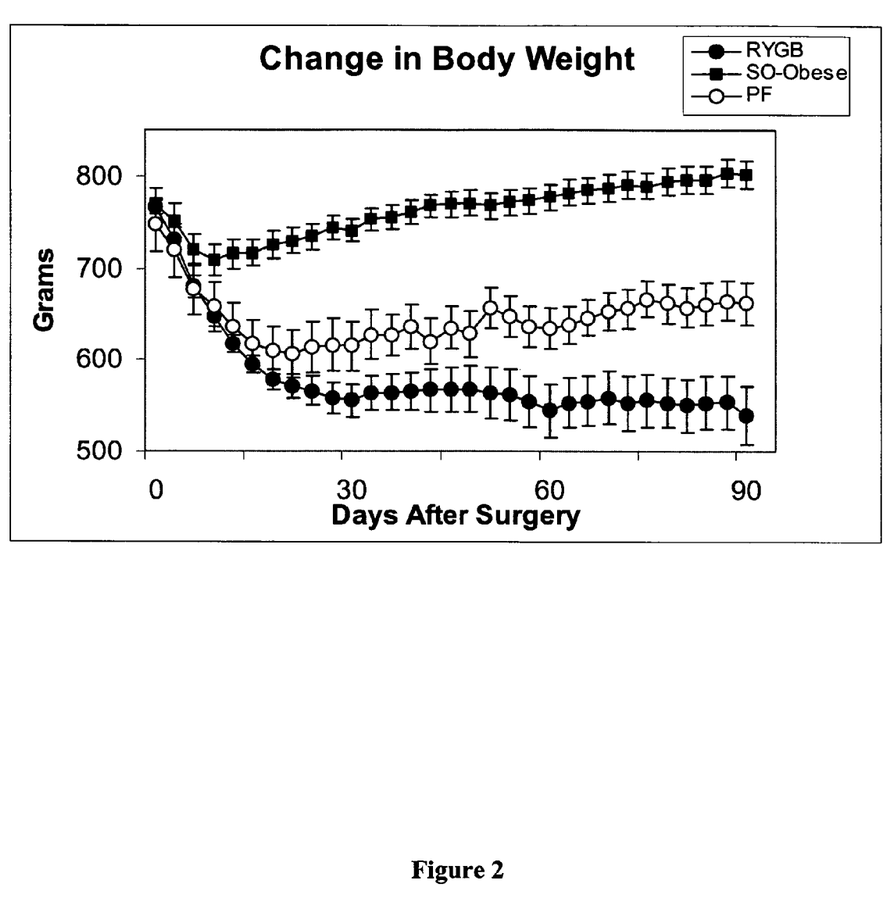
FIG. 2. After 16 wks on a high fat diet, the mean body weight of the 72 diet induced obese rats was 762±10 g. After operation a bi-phasic weight loss pattern occurred in the RYGB rats. At the end of the 90-day study the SO Obese rats weighed 801±15 g, the PF rats weighed 661±24 g and the RYGB rats weighed 538±32 g. The mean body weight change that occurred during each post-operative period is summarized in Table 1.

Daily Measurements: Postoperatively, daily body weight (BW) and caloric intake were measured each morning. The PF group was given the average food intake consumed the previous day by the RYGB group. Daily changes in BW, plotted every three day, are shown in FIG. 2 and the mean change per post-operative time periods are expressed in Table 1 using the same construct as earlier reported in our previous study (6).

Gut Hormones: SO Obese, RYGB and PF rats were decapitated under isoflurane anesthesia 14, 28 and 90 days after surgery. Mixed venous and arterial blood was tubed and centrifuged at 3,000 rpm for 10 min at 4° C. The plasma samples were stored for a limited time at −80° C. before duplicate analysis. Plasma PYY (DSL, Chicago, Ill.), ghrelin (Linco Research, St. Charles, Mo.), GLP-1 and CCK (Phoenix®, Belmont, Calif.) were measured using enzyme-immunoassay kits.

Gastric Emptying (GE): This was measured in Sham operated Control and in RYGB groups (n=6/group), 28 days after operation. Rats were food deprived for 16 h and then given pre weighed pellets for 2 h, following that food was removed for 2 h and rats were decapitated. The stomach or pouch was immediately removed, its contents desiccated and re-weighed. GE was calculated as follows: Gastric Emptying (%)=(1−[Dry Weight of Food Recovered From the Stomach (or Pouch)/Weight of Food Intake])×100 (15).

Intestinal Transit Time: This was measured in Control and RYGB groups (n=6/group), 28 days post-operatively. Rats were food deprived for 16 h and then each rat gavaged with 0.1 mL Evans Blue solution (50 mg/mL, Sigma, St. Louis, USA) into the stomach or pouch. Thirty minutes later rats were decapitated and the upper GI organs were exposed via laparotomy. The distance from the pyloric ring or the gastrojejunostomy to the most distal point of the Evans Blue in the small intestine was measured (16).

Statistical Analysis: Change in body weight, caloric intake and gut hormone data were analyzed using one-way ANOVA and multiple comparison tests by controlling the significance level individually as well as jointly at a p value of 0.05. When the ANOVA test rejected the hypothesis of no difference, the Turkey's pair-wise multiple-comparison was applied to assure that the error rate in SO Obese, RYGB and PF was equal to 0.05 jointly. To determine the inflection point of the change of daily weight after operation in each group during the 90-day study period, a switching quadratic trend analysis was conducted. This analysis allows a change of trends in average body weight of rats in each experimental group. The exact time point was estimated based on the smallest average error (s) and the highest adjusted $R^2$ for each possible time period between t=8 and t=90. It was found that the inflection points for the SO Obese, RYGB and PF groups are respectively day 9, day 34 and day 30. For the RYGB and PF groups, a switching quadratic trend model was appropriate. A switching linear trend model fit the SO Obese data well. For comparative purposes, mean body weight changes in three different time periods after surgery were calculated and summarized in Table 1. Data are expressed as Mean±SE.

TABLE 1

Mean body weight change that occurred during the post-operative period.

|  | Change-point day | Day 0 to 7 | Day 8 to change-point day | Change-point day to day 90 |
|---|---|---|---|---|
| Mean daily weight change (g) | | | | |
| SO Obese | 9 | −8.17 ± 1.37 | 3.84 | 1.06 ± 0.17 |
| RYGB | 34 | −14.27 ± 2.31 | −3.59 ± 0.50 | −0.27 ± 0.40 |
| PF | 30 | −11.59 ± 1.50 | −2.42 ± 0.98 | 0.78 ± 0.75 |
| Mean initial weight at the beginning of each period (g) | | | | |
| SO Obese | | 769 | 715 | 709 |
| RYGB | | 766 | 668 | 572 |
| PF | | 747 | 670 | 615 |

Example 3

Results and Discussion

Figure 3:
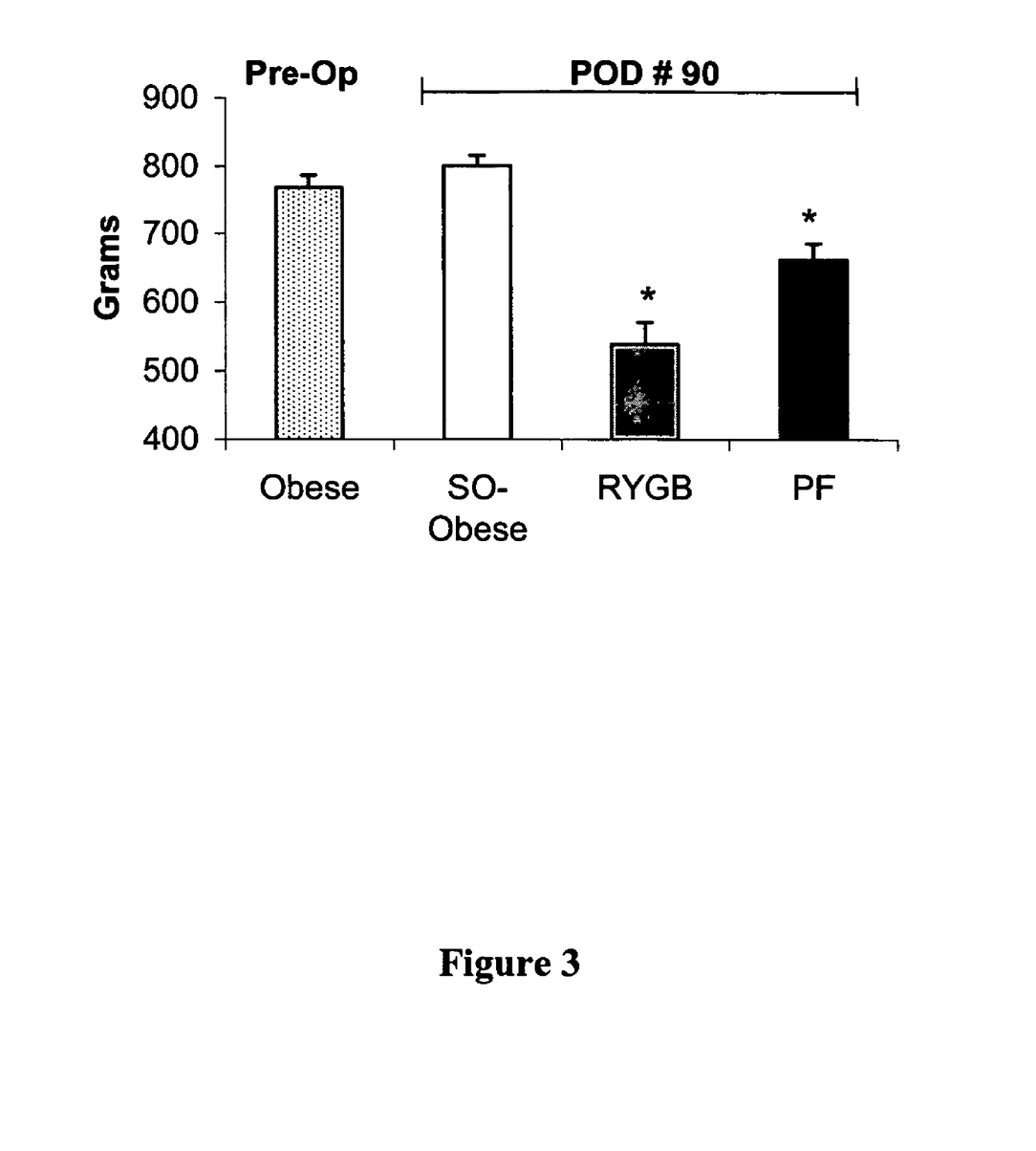
FIG. 3. Mean (±SE) differences in body weight 90 days after operations. Bar diagram-showing amount of weight loss after Roux-en-Y Gastric Bypass (RYGB; n=8), pair-fed (PF; n=8) and sham operated obese (SO obese; n=8) on 90$^{th}$ post-operative day (POD #90) and the weight of obese rats preoperatively (pre-op; n=24). *p<0.05 compared to Obese Control (SO Obese; n=8), †p<0.05 compared to PF.

Body Weight (BW): There was no significant difference in BW among the three rat groups before operation. FIG. 2 shows the changes in weight (plotted every three day) in each group of rats for the 90 post-operative days, while Table 1 summarizes the weight changes during the three time periods after operation. The SO Obese rats lost weight during the initial 7 post-operative days, because of post-operative stress and an inadequate oral liquid intake. On day 7, chow was given and SO Obese rats started to gain weight that progressively increased as indicated in FIG. 2 and Table 1. The mean weight gain of the SO Obese until day 90 was +1.06 g per day. The RYGB and PF rats also lost weight in the initial 7 post-operative days, but continued to lose weight between days 8 and change-point day. The rate of weight loss was significantly ($p<0.05$) greater in RYGB that in PF rats. During this time, the mean rate of weight loss for the RYGB was −5.7 g per day, while that for the PF was −4.4 g per day. After change-point day, PF rats steadily gained weight at a mean of +0.78 g per day, while RYGB rats lost weight at a mean of −0.27 g per day. By day 90, RYGB had lost 33% BW as compared to SO Obese rats ($p<0.05$) and PF rats had lost 17% BW as compared to SO Obese rats ($p<0.05$), as shown in FIG. 3. Body weight in RYGB rats was 538±32 g, which was significantly less than SO Obese rats (801±15 g), and than PF rats (661±24 g).

Figure 4:
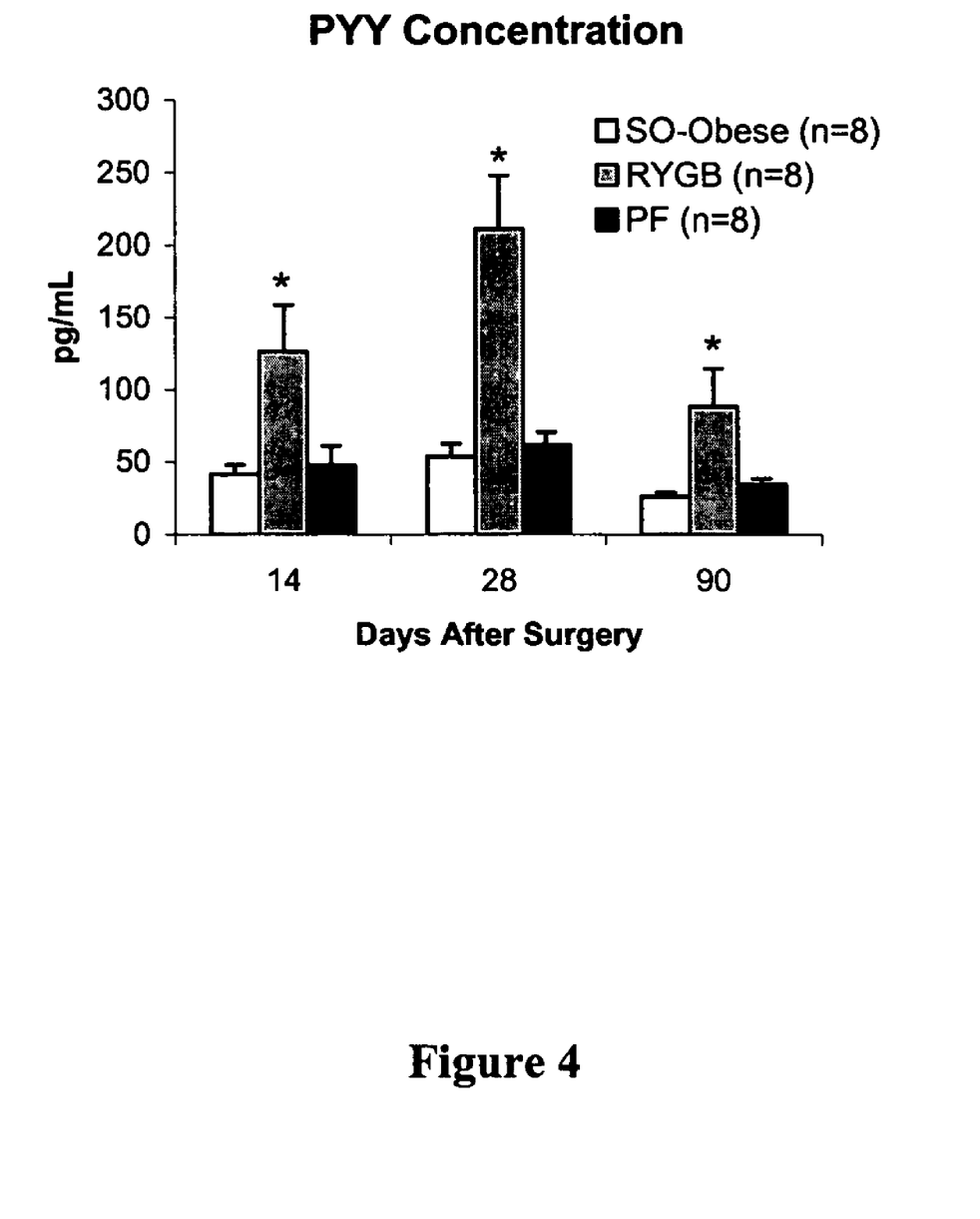
FIG. 4. Peptide YY (PYY) concentrations at 14, 28 and 90 days after surgery. *p<0.05 compared to SO-Obese and PF, † p<0.05 compared to 14 days and 90 days after surgery.

Gut Hormones: The concentrations of gut hormones on the 90th post-operative day are shown in Table 2. In comparing RYGB rats with SO Obese and PF rats, plasma ghrelin was significantly lower ($p<0.05$), while plasma PYY was significantly higher ($p<0.05$). There were no significant differences in plasma CCK and GLP-1 between the three groups. As shown in FIG. 4, plasma PYY concentrations in RYGB rats at 14, 28 and 90 days after surgery were 126.3±32.1 pg/mL, 211.0±36.8 pg/mL and 88.3±26.3 pg/mL, respectively. On each day, PYY concentrations in RYGB rats were significantly greater than in SO Obese and in PF rats. PYY concentrations were also highest ($p<0.05$) on day 28 versus days 14 and 90.

Figure 5A:
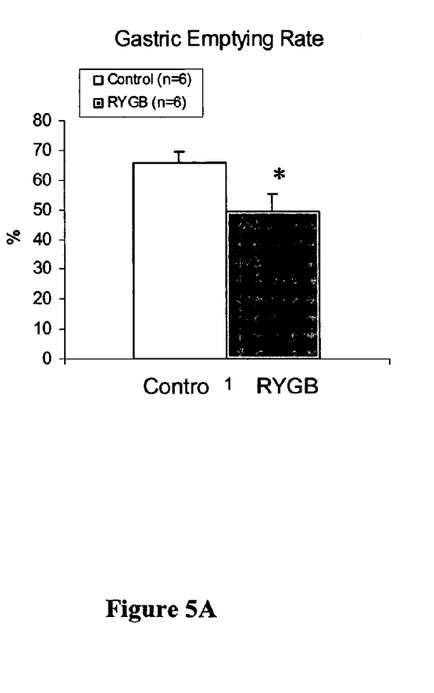
Figure 5B:
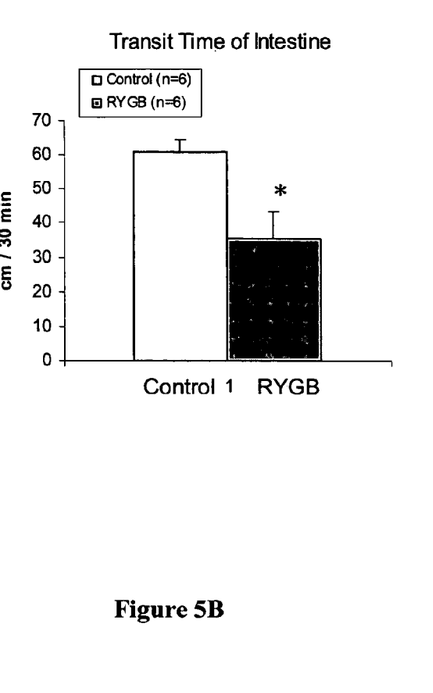

Gastrointestinal emptying (GE) and Intestinal transit time (ITT): GE rate in RYGB rats (49.5±5.8%) was significantly slower than Control rats (65.9±5.8%) (FIG. 5A). ITT rate in 30 minutes was 35.5±7.8 cm in RYGB rats, while it was significantly faster in Control rats (60.9±3.6 cm) ($p<0.05$) (FIG. 5B).

TABLE 2

GI hormonal changes 90 days after surgery

| GI Hormone | SO Obese (n = 8) | RYGB (n = 8) | PF (n = 8) |
|---|---|---|---|
| PYY (pg/mL) | 25.9 ± 3.0 | 88.3 ± 26.3* | 34.9 ± 3.5 |
| Ghrelin (fmol/ml) | 12.3 ± 1.9 | 6.5 ± 0.8* | 14.8 ± 2.7 |
| CCK (ng/mL) | 0.25 ± 0.06 | 0.21 ± 0.04 | 0.16 ± 0.01 |
| GLP-1 (ng/mL) | 0.51 ± 0.05 | 0.56 ± 0.04 | 0.51 ± 0.03 |

*RYGB vs. SO Obese and PF, $p < 0.05$.

Discussion—The endocrine L cells secrete PYY in response to intraluminal nutrients. These cells are found in progressively higher gradient concentration from the duodenum and jejunum where PYY is released at relatively lower concentrations, to the terminal ileum and the colon where PYY is secreted in high concentrations (17). PYY's biological function includes inhibition of food intake, decreasing gastric emptying and slowing GI motility (18,19).

Ninety days after operation, the SO Obese rats weighed more than before operation and had a PYY concentration of 25.9±3.0 pg/mL. In contrast, the RYGB rats had lost 33% body weight and had a significantly higher PYY concentration of 88.3±26.3 relative to the SO Obese rats. Yet the PF rats, which were fed the same amount of daily food as the RYGB rats, had lost only 17% body weight although their PYY concentrations were similar to the SO Obese rats. The data of the RYGB rats could be interpreted to reflect the early and direct entrance of food into the hindgut, leading to a persistently high physiological PYY level over a prolonged period of time, therefore contributing to the significantly greater weight loss during the 90 days after operation. This interpretation is supported by the findings in the PF rats. Ninety days after the operation, the PF rats had lost less weight than the RYGB rats, and the PYY concentrations in the PF rats were the same as in the SO Obese rats. These results with the PF rats could be explained by that the PF rats have an intact GI tract, and although they were fed the equivalent amount of food as the RYGB rats, more intraluminal nutrients were absorbed in the foregut and less passed into the hindgut to stimulate the higher volume of L cells secreting PYY. Thus, it is believed that the re-arranged anatomy subsequent to the RYGB plays a critical role in facilitating the rapid secretion of PYY and in determining the protracted weight loss after RYGB.

In contrast to the 90 days data described above, a single intraperitoneal injection of $PYY_{(3-36)}$ to 24 h fasted mice resulted in a significant reduction of food intake for 24 h but not for 48 h, while in freely feeding mice food intake was unchanged by PYY (20). Administration of $PYY_{(3-36)}$ decreased ad libitum food intake by 33% per meal in 12 obese subjects, as compared to 12 lean subjects (21). The effect of PYY occurs via vagally and hormonally mediated signals to hypothalamic appetite regulatory neurons, where PYY acts by binding to Y2-R pre-synaptic inhibitory receptors that are abundantly expressed on neuropeptide Y (NPY) neurons in the arcuate nucleus (22) to decrease food intake, and inhibit gastric emptying and intestinal transit (18,23).

In rodents, conflicting results of both the peripheral and central administration of $PYY_{(3-36)}$ on food intake and body weight have been reported (24,25). Nevertheless, the significance of PYY in RYGB has been demonstrated herein because elevated PYY levels occurred as early as 14 days after re-arranging the GI tract, suggesting that the diversion of food into the hindgut is a major contributory factor in regulating food intake. Furthermore, the concentration of PYY peaked at POD 28 (FIG. 4), which corresponded temporally to the period of most dynamic reduction in body weight. At 28 days when the PYY concentrations were higher than at 14 or 90 days (FIG. 4), gastric emptying rate and intestinal transit time were both significantly delayed (FIGS. 5A-5B). The combined factors contributed to the cumulative weight loss in RYGB, which was more significant than PF and SO Obese rats. Postprandial PYY concentrations have been reported as elevated in humans at 35 months after RYGB (26).

By creating a small gastric pouch, and by diverting food away from the rest of the stomach and proximal small intestine where most of the X/A ghrelin secreting cells are located, food is prevented from stimulating ghrelin, whose concentrations increase markedly before and decrease after each meal. Normally, ghrelin is both vagally and hormonally sensed by the hypothalamic arcuate nucleus where it activates neurons that secrete NPY, mediated by agouti-related peptide (AgRP), to stimulate food intake and promote weight gain (27,28,29). Ghrelin also inhibits serotonin release in the brain, which usually inhibits food intake (30). Thus, the anatomical re-arranging of the GI tract eliminates the usual food intake stimulatory effect of ghrelin leading instead to a decrease in appetite and food intake, which persists even 90 days post-RYGB. In contrast, ghrelin was shown to remain elevated in the GI intact SO Obese and PF rats at 90 days (Table 2). If one accepts the premise that 10 rat days are approximately equal to one human year, based on the data presented hereinabove on RYGB rats, one would expect to find low ghrelin concentrations in long-term follow-up studies after RYGB in patients with protracted weight loss.

As shown in Table 2, there were no significant differences in cholecystokinin (CCK) among the three groups of rats. The enteroendocrine cells of the duodenal and jejunal mucosa secrete CCK in response to intraluminal nutrients, following which there is a rapid rise within 10-30 minutes after a meal, which remains elevated 3-5 h after eating. The activated CCK receptors in vagal afferent fibers transmit a sensation of fullness in the dorsomedial hypothalamus (36) suppressing NPY and providing an important feedback signal for decreasing meal size and meal duration. These play a major role in the sensation of satiation (37). CCK also stimulates intestinal motor activity resulting in pyloric contraction thereby inhibiting gastric emptying and modulating intestinal motility (38). The result observed in this application is in agreement with earlier reports that CCK is not significantly changed by RYGB in humans (26,39).

Glucagon-like peptide-1 (GLP-1) was also unchanged 90 days after RYGB. GLP-1 is mostly produced by L-cells in the distal small intestine and colon (18) and significantly improves or even restores normal glucose-induced insulin secretion in diabetic patient (40). There have been several reports in morbidly obese humans in which GLP-1 was increased 12 weeks after RYGB (41,42). The differences between these human data and the rat data described in this application may be due to the length of biliopancreatic (BP) limb in the rat model.

In sum, the results obtained in the present studies show that ninety days after RYGB, an increase in PYY and a decrease in ghrelin occurred, resulting at least in part loss of hunger sensation, decreased food intake and decrease in GI motility, which is believed to contribute to weight loss.

Example 4

Figure 6:
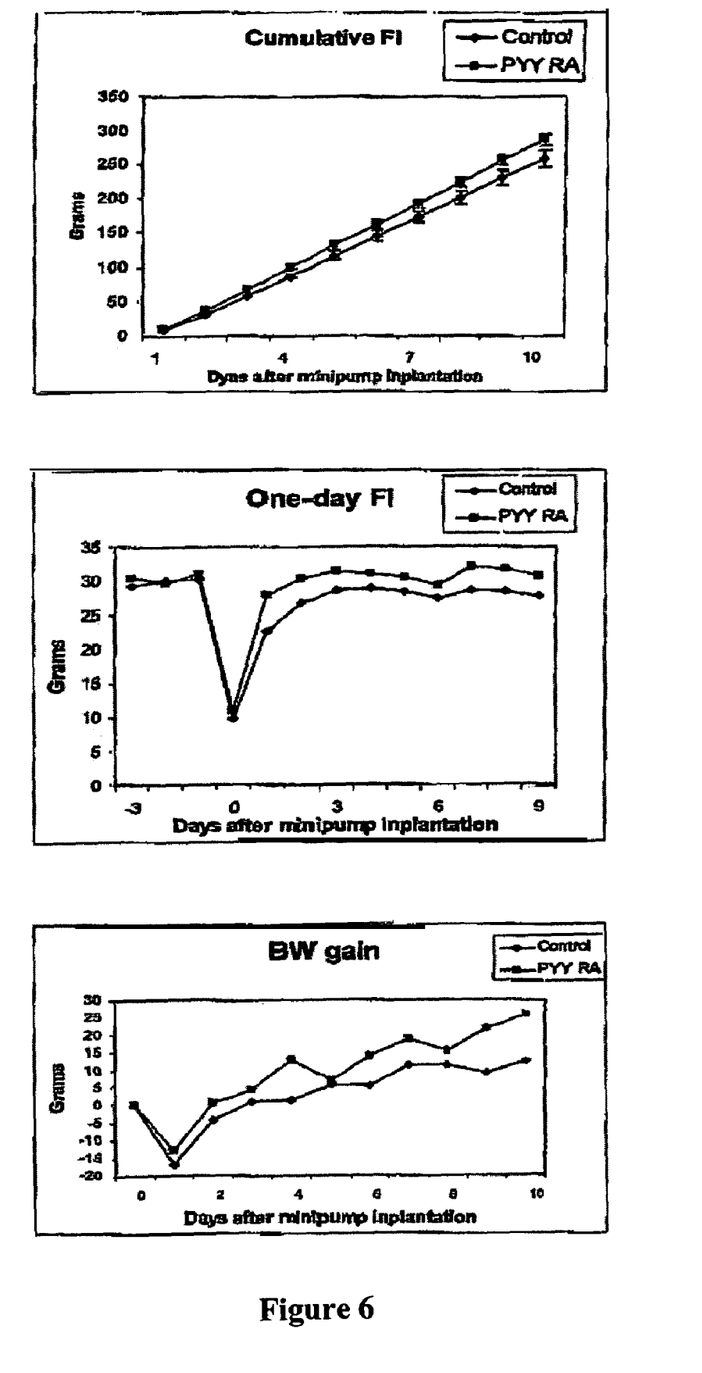
FIG. 6. Daily and cumulative food intake and body weight of RYGB rats given a PYY receptor antagonist via an implanted intraperitoneal pump.

A pump (Model 2002, Alza Corp. Palo Alto, Calif.) was implanted i.p. in each of 5 RYGB rats thirty days after RYGB. The pump was loaded with either the PYY receptor antagonist, B11E0246 (TOCRIS, Ellisville, Mo.), or a control solution (DMSO), and released its ingredient at the rate of about 8.3 µl/day (360 nm B11E0246/Kg/day). Food intake was measured as described above. As shown in FIG. 6, the PYY receptor antagonist to RYGB rats which had lost weight after RYGB increased daily and cumulative food intake.

Figure 7:
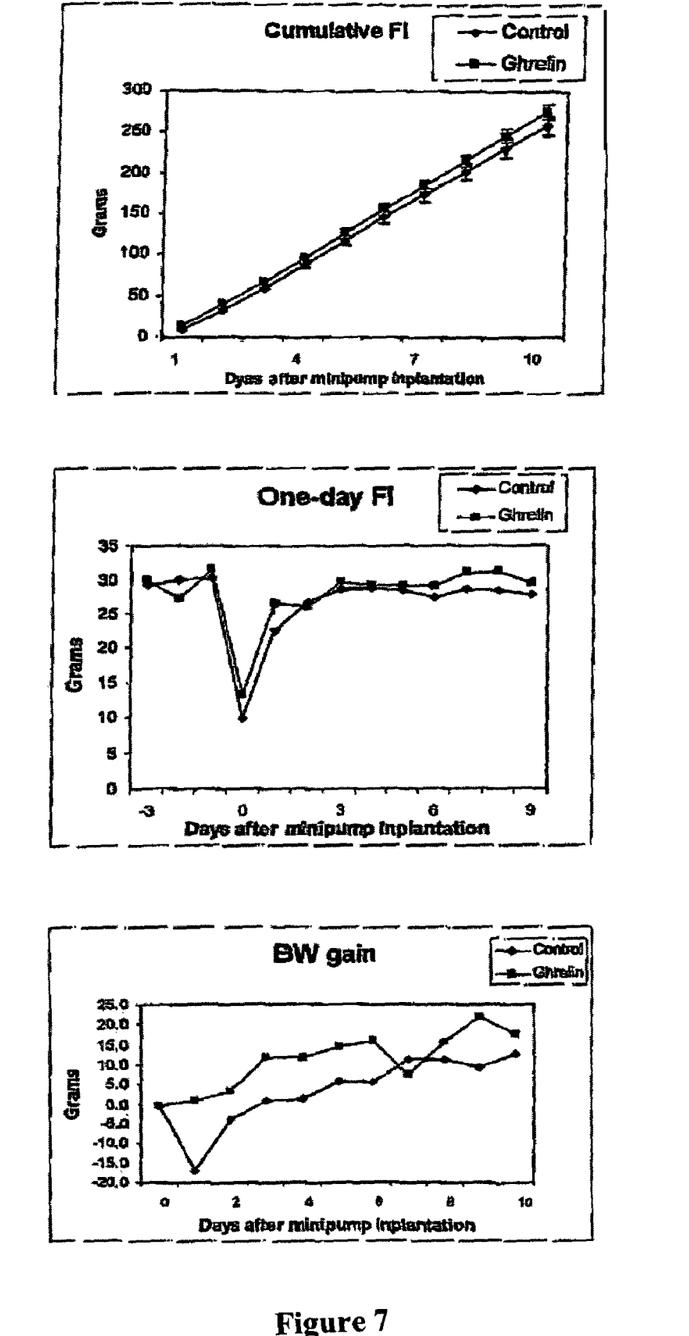
FIG. 7. Daily and cumulative food intake and body weight of RYGB rats given ghrelin via an implanted intraperitoneal pump.

In a second experiment, a pump was implanted i.p. in each of 5 RYGB rats thirty days after RYGB. The pump was loaded with either ghrelin, or a control solution (DMSO), and released its ingredient at the rate of 8.3 µl/day (60 ng ghrelin/Kg/day). Food intake was measured as described above. The results are shown in FIG. 7.

In a third experiment, a pump was implanted i.p. in each of 5 RYGB rats thirty days after RYGB. The pump was loaded with either a combination of the PYY receptor antagonist B11E0246 and ghrelin, or a control solution (DMSO). The pump released its ingredient at the rate of 8.3 µl/day (360 nm B11E0246/Kg/day and 60 ng ghrelin/Kg/day). Food intake was measured as described above.

REFERENCES

1. Buchwald H, Avidor Y, Braunwald E, Jensen M D, Pories W, Fahrbach K, et al. Bariatric surgery: a systematic review and meta-analysis. JAMA 2004; 292:724-37.
2. Brolin R E. Bariatric surgery and long-term control of morbid obesity. JAMA 2002; 288:2793-6.
3. Schauer P R, Burguera B, Ikramuddin S, Cottam D, Gourash W, Hamad G, et al. Effect of laparoscopic Roux-en Y gastric bypass on type 2 diabetes mellitus. Ann Surg 2003; 238:467-84.
4. Sarr M G. Open Roux-en-Y gastric bypass: indications and technique. J Gastrointest Surg 2004; 8:390-2.

5. MacLean L D, Rhode B M, Nohr C W. Late outcome of isolated gastric bypass. Ann Surg 2000; 231:524-8.
6. Meguid M M, Ramos E J, Suzuki S, Xu Y, George Z M, Das U N, et al. A surgical rat model of human roux-en-Y gastric bypass. J Gastrointest Surg 2004; 8:621-30.
7. Halmi K A, Mason E, Falk J R, Stunkard A. Appetitive behavior after gastric bypass for obesity. Int J Obes 1981; 5:457-64.
8. Xu Y, Ohinata K, Meguid M M, Marx W, Tada T, Chen C, et al. Gastric bypass model in the obese rat to study metabolic mechanisms of weight loss. J Surg Res 2002; 107: 56-63.
9. Ramos E J, Xu Y, Romanova I, Middleton F, Chen C, Quinn R, et al. Is obesity an inflammatory disease? Surgery. 2003; 34:329-35.
10. Meguid M M, Laviano A, Rossi-Fanelli F. Food intake equals meal size times mean number. Appetite 1998; 31:404.
11. Grill H J, Kaplan J M. The neuroanatomical axis for control of energy balance. Front Neuroendocrinol 2002; 23:2-40.
12. Middleton F A, Ramos E J, Xu Y, Diab H, Zhao X, Das U N, et al. Application of genomic technologies: DNA microarrays and metabolic profiling of obesity in the hypothalamus and in subcutaneous fat. Nutrition 2004; 20:14-25.
13. Romanova I V, Ramos E J, Xu Y, Quinn R, Chen C, George Z M, et al. Neurobiologic changes in the hypothalamus associated with weight loss after gastric bypass. J Am Coll Surg 2004; 199:887-95.
14. Pories W J, Swanson M S, MacDonald K G, Long S B, Morris P G, Brown B M, et al. Who would have thought it? An operation proves to be the most effective therapy for adult-onset diabetes mellitus. Ann Surg 1995; 222:339-50.
15. Asakawa A, Inui A, Kaga T, Yuzuriha H, Nagata T, Ueno N, et al. Ghrelin is an appetite-stimulatory signal from stomach with structural resemblance to motilin. Gastroenterology 2001; 120:337-45.
16. Qin X Y, Lei Y, Liu F L. Effects of two methods of reconstruction of digestive tract after total gastrectomy on gastrointestinal motility in rats. World J Gastroenterol 2003; 9:1051-3.
17. Adrian T E, Ferri G L, Bacarese-Hamilton A J, Fuessl H S, Polak J M, Bloom S R. Human distribution and release of a putative new gut hormone, peptide YY. Gastroenterology 1985; 89:1070-7.
18. Fujimiya M, Inui A. Peptidergic regulation of gastrointestinal motility in rodents. Peptides 2000; 21:1565-82.
19. Savage A P, Adrian T E, Carolan G, Chatterjee V K, Bloom S R. Effects of peptide YY (PYY) on mouth to caecum intestinal transit time and on the rate of gastric emptying in healthy volunteers. Gut 1987; 28:166-70.
20. Challis B G, Pinnock S B, Coll A P, Carter R N, Dickson S L, O'Rahilly S. Acute effects of PYY3-36 on food intake and hypothalamic neuropeptide expression in the mouse. Biochem Biophys Res Commun 2003; 311:915-9.
21. Korner J, Leibel R L. To eat or not to eat—how the gut talks to the brain. N Engl J Med 2003; 349:926-8.
22. Broberger C, Landry M, Wong H, Walsh J N, Hokfelt T. Subtypes Y1 and Y2 of the neuropeptide Y receptor are respectively expressed in pro-opiomelanocortin- and neuropeptide-Y-containing neurons of the rat hypothalamic arcuate nucleus. Neuroendocrinology 1997; 66:393-408.
23. Batterham R L, Cowley M A, Small C J, Herzog H, Cohen M A, Dakin C L, et al. Gut hormone PYY (3-36) physiologically inhibits food intake. Nature 2002; 418:650-4.
24. Tschop M, Castaneda T R, Joost H G, Thone-Reineke C, Ortmann S, Klaus S, et al. Does gut hormone PYY3-36 decrease food intake in rodents? Nature 2004; 430:165.
25. Batterham R L, Cowley M A, Small C J, Herzog H, Cohen M A, Dakin C L, et al. Reply to communication from reference 24. Nature 2004; 430:165.
26. Korner J, Bessler M, Cirilo L, Conwell I M, Daud A, Restuccia N L, et al. Effects of Roux-en-Y Gastric Bypass Surgery on Fasting and Postprandial Concentrations of Plasma Ghrelin, PYY and Insulin. J Clin Endocrinol Metab 2005; 90:359-65.
27. Brunetti L, Recinella L, Orlando G, Michelotto B, Di Nisio C, Vacca M. Effects of ghrelin and amylin on dopamine, norepinephrine and serotonin release in the hypothalamus. Eur J Pharmacol 2002; 454:189-92.
28. Date Y, Murakami N, Toshinai K, Matsukura S, Niijima A, Matsuo H, et al. The role of the gastric afferent vagal nerve in ghrelin-induced feeding and growth hormone secretion in rats. Gastroenterology 2002; 123:1120-8.
29. Tschop M, Statnick M A, Suter T M, Heiman M L. GH-releasing peptide-2 increases fat mass in mice lacking NPY: indication for a crucial mediating role of hypothalamic agouti-related protein. Endocrinology. 2002; 143: 558-68.
30. Laviano A, Meguid M M. Serotonin and Obesity. Curr Med Chem—Central Nervous System Agents 2003; 3:89-100.
31. Cummings D E, Shannon M H. Ghrelin and gastric bypass: is there a hormonal contribution to surgical weight loss? J Clin Endocrinol Metab 2003; 88:2999-3002.
32. Geloneze B, Tambascia M A, Pilla V F, Geloneze S R, Repetto E M, Pareja J C. Ghrelin: a gut-brain hormone: effect of gastric bypass surgery. Obes Surg 2003; 13:17-22.
33. Cummings D E, Weigle D S, Frayo R S, Breen P A, Ma M K, Dellinger E P, et al. Plasma ghrelin levels after diet-induced weight loss or gastric bypass surgery. N Engl J Med 2002; 346:1623-30.
34. Leonetti F, Silecchia G, Iacobellis G, Ribaudo M C, Zappaterreno A, Tiberti C, et al. Different plasma ghrelin levels after laparoscopic gastric bypass and adjustable gastric banding in morbid obese subjects. J Clin Endocrinol Metab 2003; 88:4227-31.
35. Holdstock C, Engstrom B E, Ohrvall M, Lind L, Sundbom M, Karlsson F A. Ghrelin and adipose tissue regulatory peptides: effect of gastric bypass surgery in obese humans. J Clin Endocrinol Metab 2003; 88:3177-83.
36. Blevins J E, Stanley B G, Reidelberger R D. Brain regions where cholecystokinin suppresses feeding in rats. Brain Res 2000; 860:1-10.
37. Gibbs J, Young R C, Smith G P. Cholecystokinin decreases food intake in rats. J Comp Physiol Psychol 1973; 84:488-95.
38. Moran T H, McHugh P R. Cholecystokinin suppresses food intake by inhibiting gastric emptying. Am J Physiol 1982; 242:R491-7.
39. Kellum J M, Kuemmerle J F, O'Dorisio T M, Rayford P, Martin D, Engle K, et al. Gastrointestinal hormone responses to meals before and after gastric bypass and vertical banded gastroplasty. Ann Surg 1990; 211:763-70
40. Nauck M A, Heimesaat M M, Orskov C, Holst J J, Ebert R, Creutzfeldt W. Preserved incretin activity of glucagon-like peptide 1 [7-36 amide] but not of synthetic human gastric inhibitory polypeptide in patients with type-2 diabetes mellitus. J Clin Invest 1993; 91:301-7.

41. Clements R H, Gonzalez Q H, Long C I, Wittert G, Laws H L. Hormonal changes after Roux-en Y gastric bypass for morbid obesity and the control of type-II diabetes mellitus. Am Surg 2004; 70:1-4.

42. Patriti A, Facchiano E, Sanna A, Gulla N, Donini A. The enteroinsular axis and the recovery from type 2 diabetes after bariatric surgery. Obes Surg 2004; 14:840-8.

What is claimed is:

1. A pharmaceutical composition for reducing body weight or rate of weight gain, comprising an effective amount of a combination of (a) one or more of PYY, a peptide consisting of amino acid 3 to 36 of a human PYY, $PYY_{3-36}$, $PYY_{22-36}$, BIM-43004, BIM-43073D, BIM-43004C, N-α-Ac-[Phe$^{27}$]PYY(22-36), N-α-Ac-[TRP27]PYY(22-36), N-α-Ac-[Thi$^{27}$]PYY(22-36), N-α-Ac-[Tyr$^{22}$, Phe$^{27}$]PYY(22-36), [Im-DNP-His$^{26}$]PYY, PYY(22-36), [Ala$^{32}$]PYY(22-36), [Ala$^{23,32}$]PYY(22-36), [Glu$^{28}$]PYY(22-36), N-α-Ac-PYY(22-36), N-α-Ac-[p.Cl-Phe$^{27}$]PYY(22-36), N-α-Ac-[Glu$^{26}$]PYY(22-36), N-α-Ac-[N-Me-Tyr$^{36}$]PYY(22-36), N-α-Myristoyl-PYY(22-36), N-α-Naphthaleneacetyl-PYY(22-36), N-α-Ac-[Phe$^{27}$]PYY(22-36), N-α-Ac-[Bth$^{27}$]PYY(22-36), N-α-Ac-[Bip$^{27}$]PYY(22-36), N-α-Ac-[Nal$^{27}$]PYY(22-36), N-α-Ac-[Tic$^{27}$]PYY(22-36), N-α-Ac-[Phe$^{27}$]PYY(25-36), N-α-Ac-[Trp$^{27}$]PYY(22-36), PYY(13-36), NPY(13-36), and (b) a ghrelin.

2. The pharmaceutical composition of claim 1, wherein said PYY is human PYY.

3. The pharmaceutical composition of claim 1, wherein said ghrelin is recombinant human ghrelin.

4. A method for reducing the body weight or the rate of weight gain in a subject, comprising administering a pharmaceutical composition according to any one of claim 1, 2 or 3 to said subject.

5. A method for treating obesity or an obesity-related disorder in a subject, comprising administering a pharmaceutical composition according to any one of claim 1, 2 or 3 to said subject.

6. The method of claim 5, wherein said obesity-related disorder is diabetes.

7. A pharmaceutical composition for increasing the body weight or decreasing the rate of weight loss in a subject, comprising an effective amount of a combination of an antagonist of PYY or PYY receptor with a ghrelin.

8. The pharmaceutical composition of claim 7, wherein said antagonist is B11E0246.

9. The pharmaceutical composition of claim 7, wherein said ghrelin is recombinant human ghrelin.

10. A method for increasing the body weight or decreasing the rate of weight loss in a subject, comprising administering to said subject a pharmaceutical composition according to any one of claims 7-9.

* * * * *